US00PP08390P

United States Patent [19]

Meilland

[11] Patent Number: Plant 8,390

[45] Date of Patent: Sep. 28, 1993

[54] ROSE PLANT—MEINIMO VARIETY

[75] Inventor: Alain A. Meilland, Antibes, France

[73] Assignee: The Conard-Pyle Company, West Grove, Pa.

[21] Appl. No.: 921,065

[22] Filed: Jul. 29, 1992

[51] Int. Cl.[5] ..... A01H 5/00
[52] U.S. Cl. ..... Plt./18
[58] Field of Search ..... Plt. 18, 20, 19, 11

*Primary Examiner*—Howard J. Locker
*Attorney, Agent, or Firm*—Burns, Doane, Swecker & Mathis

[57] ABSTRACT

A new and distinct variety of Hybrid Tea rose plant is provided which abundantly and continuously forms attractive fully double very long lasting blossoms which exhibit a very soft and delicate Dawn Pink coloration. The blossoms exhibit a spicy fragrance. The plant exhibits a bushy growth habit, reddish-brown adult wood, forms vigorous and strong vegetation, and is well suited for service as attractive ornamentation in parks and gardens. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meigurami variety (nonpatented in the United States). The male parent (i.e., the pollen parent) was the product of the cross of the Meinaregi variety (nonpatented in the United States) and the Meidragelac variety (nonpatented in the United States). The parentage of the new variety can be summarized as follows:

Meigurami × (Meinaregi × Meidragelac).

The seeds resulting from the above pollination were sown and 234 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive very long lasting fully double blossoms which exhibit a soft and delicate Dawn Pink coloration,
(b) forms blossoms which exhibit a spicy fragrance,
(c) forms reddish-brown adult wood,
(d) exhibits strong and vigorous vegetation,
(e) exhibits a bushy growth habit,
(f) is particularly suited for growing in parks and gardens, and
(g) is not particularly affected by cryptogamic diseases.

The new variety well meets the needs of the horticultural industry and is particularly well suited for use as attractive ornamentation in the landscape.

The new variety has been found to undergo asexual propagation by a number of routes, including budding, grafting, cuttage, etc. Asexual propagation by the above-mentioned methods as performed in France has shown that the characteristics of the new variety are strictly transmissible from one generation to another.

The new variety has been named the Meinimo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing outdoors at LeCannet-des-Maures, Var, France.

FIG. 6 illustrates a specimen of an open flower—plan view—obverse;

DETAILED DESCRIPTION

Figures 1, 2, 3, 4, 5, 7, 8, 9, 10, 11, 12, 13, 14, 15, 16:
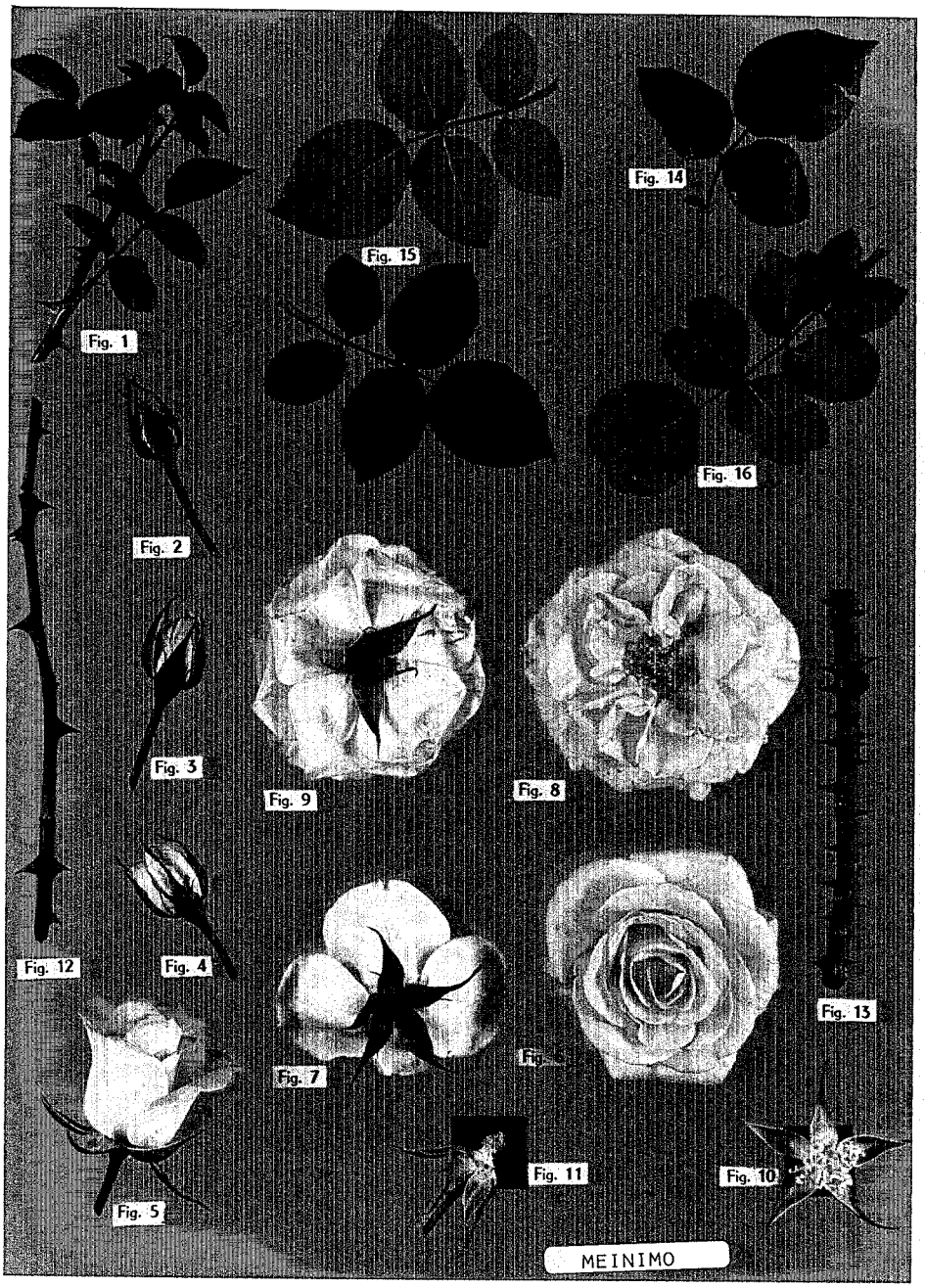
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates specimens of leaves with five leaflets—plan view—under surface (top) and upper surface (bottom)
FIG. 16 illustrates a specimen of a leaf with seven leaflets—plan view—under surface.

The chart used in the identification of the colors is that of The Royal Horticultural Society (R.H.S. Colour Chart). The description is based on the observation of two year old plants made during June while budded on *Rosa froebelli* understock and growing in outdoors at LeCannet-des-Maures, Var, France. The coloration in common terms precedes reference to the chart.

Class: Hybrid Tea.

Plant:

*Height.*—Approximately 90 cm. on average

*Habit.*—Bushy.

Branches:

*Color.*—Young stems: reddish. Adult wood: reddish-brown.

*Thorns.*—Size: large. Quantity: numerous. Color: reddish on young stems and greenish changing to tan on mature wood.

Leaves:

*Stipules.*—Adnate, pectinate, narrow and linear.

*Petioles.*—Upper surface: striped reddish brown on young foliage and medium green on mature foliage with very glandular edges. Under surface: light green, and bear a few prickles.

*Leaflets.*—Number: 3, 5, and 7. Shape: oval. Serration: single and regular. Texture: leathery. General appearance: dense, matte foliage. Color (young foliage): Upper surface: bronze green, Yellow-Green Group 146A. Under surface: light green, Yellow-Green Group 146C. Color (adult foliage): Upper surface: dark green, Yellow-Green Group 147A. Under surface: medium green, Yellow-Green Group 147B.

Inflorescence:

*Number of flowers.*—Usually one single bloom per stem; however, up to three blooms per stem sometimes are formed.

*Peduncle.*—Medium green, straight, and rigid. The length is approximately 5 to 8 cm. on average.

*Sepals.*—Upper surface: Tomentose, greenish and widely suffused with reddish coloration. Under surface: light green and widely suffused with reddish coloration.

Buds.—Shape: ovoid. Length: approximately 3 cm. on average. Size: medium. Color upon opening: Upper surface: Mandarin Red, Red Group 40C, edged and suffused with Azalea Pink, Red Group 38A. Under surface: peach, Orange Group 29C.

*Flower.*—Shape: elongated and turning into a flat cup when fully open, fully double. Diameter: approximately 9 cm. on average. Color (when opening begins): Upper surface: Azalea Pink, Red Group 38A. Under surface: Coral Pink, Red Group 38D. Color (when blooming): Upper surface: Dawn Pink, Red Group 49A. Under surface: light Venetian Pink, Red Group 49C. Color (at end of opening): Upper surface: Dawn Pink, Red Group 49A. Under surface: light Venetian Pink, Red Group 49C. Fragrance: spicy. Lasting quality: very long lasting bloom when on the plant or when cut and placed in a vase. Petal number: approximately 32 to 35 on average. Petal shape: rounded. Texture: very consistent. Petal drop: fairly good. Stamen number: approximately 138 to 143 on average. Anthers: ochre, normal. Filaments: bright yellow in coloration and of irregular heights. Pistils: approximately 78 to 84 on average. Stigmas: normal, straw colored. Styles: straw colored with fuchsine tips and of irregular height. Receptacle: medium green, more or less suffused with reddish coloration, in longitudinal section at the dehiscence of the anthers it is wide and in the shape of a pitcher.

Development:

*Vegetation.*—Vigorous and strong.

*Blooming.*—Abundant and continuous throughout the growing season.

*Aptitude to bear fruits.*—Normal.

*Resistance to frost.*—Normal.

*Resistance to diseases.*—Very good.

I claim:

1. A new and distinct variety of Hybrid Tea rose plant characterized by the following combination of characteristics:

(a) forms in abundance on a continuous basis attractive very long lasting fully double blossoms which exhibit a soft and delicate Dawn Pink coloration,
(b) forms blossoms which exhibit a spicy fragrance,
(c) forms reddish-brown adult wood,
(d) exhibits strong and vigorous vegetation,
(e) exhibits a bushy growth habit,
(f) is particularly suited for growing in parks and gardens, and
(g) is not particularly affected by cryptogamic diseases;

substantially as herein shown and described.

* * * * *

MEINIMO